United States Patent
Franchi

(10) Patent No.: US 7,988,910 B2
(45) Date of Patent: Aug. 2, 2011

(54) METHOD OF DISINFECTING AND WETTING THE INTERIOR OF A BUILDING

(76) Inventor: Richard Michael Franchi, Derby, CT (US)

( * ) Notice: Subject to any disclaimer, the term of this patent is extended or adjusted under 35 U.S.C. 154(b) by 0 days.

(21) Appl. No.: 12/006,223

(22) Filed: Jan. 2, 2008

(65) Prior Publication Data

US 2009/0169424 A1    Jul. 2, 2009

(51) Int. Cl.
*A61L 2/16* (2006.01)
(52) U.S. Cl. ............... 422/28; 422/29; 422/37; 422/120
(58) Field of Classification Search ............... 422/28, 422/29, 37, 120, 123
See application file for complete search history.

(56) References Cited

U.S. PATENT DOCUMENTS

| | | | | |
|---|---|---|---|---|
| 2003/0143111 | A1* | 7/2003 | Cowley et al. | 422/37 |
| 2006/0008379 | A1* | 1/2006 | Mielnik et al. | 422/32 |
| 2006/0228253 | A1* | 10/2006 | Mason | 422/32 |
| 2008/0310997 | A1* | 12/2008 | Centanni et al. | 422/30 |

\* cited by examiner

*Primary Examiner* — Sean E Conley

(57) ABSTRACT

A method of disinfecting and wetting the inside of a building and articles therein at or about one atmospheric pressure which involves the steps of sealing the interior of the building, then conditioning the air inside of the building to a specific temperature and humidity, then heating said air and introducing any of a number of anti-bacterial agents in aqueous solution into said air until a higher specific temperature and humidity are achieved causing the air to be disinfected then optionally condensing the humid air and antibacterial agent until all of the interior surfaces are wetted and disinfected and condensing water vapor onto the interior surfaces then evaporating the liquid wetting said surfaces then condensing said vapor into a disposal tank or sewer and then condensing water again onto the interior surfaces and evaporating it then disposing of the vaporized water.

6 Claims, No Drawings

METHOD OF DISINFECTING AND WETTING THE INTERIOR OF A BUILDING

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOIN RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of Invention

The instant invention relates to a novel method and means for the efficient, safe, and economic decontamination of the interior of a physical structure, such as a building, and/or articles contained therein that are contaminated by microorganisms.

2. Description of Related Art

U.S. Pat. No. 5,044,141 disclosed a method for the sterile packaging and wetting of articles in a bottle, bag, or other sealable container utilizing a solution, usually but not necessarily an aqueous solution, of a standard anti-bacterial agent. The method allows for partially filling the container with such a solution, and placing in the container those items to be sterilized then the container is sealed so that an air (or gas) space is formed above the liquid. Thereafter the container and its contents are heated to a temperature well below the boiling point of the liquid and at a pressure of about one atmosphere. The heating operation is continued until all organisms, including spores, are killed. Finally, the container and its contents are cooled to below the dew point of the air (or gas) so as to allow the humidified air (or gas), as produced during the heating step, to condense the solution on to the surfaces inside the container which are in the air space and not submerged under the liquid solution. The cooling operation depends upon the heating operation because the dew point temperature is relative to the humidity and temperature of the air (or gas) in the space which is created by the heated air (or gas).

U.S. Pat. No. 5,345,746 disclosed a method of regulating the amount of anti-bacterial agent present in the air space inside a container during the sterilization processes as disclosed in U.S. Pat. No. 3,857,677, U.S. Pat. No. 3,725,003 and U.S. Pat. No. 5,044,141. The sterilization process required the container and all its contents to be heated in order for the sterilization to take place. The U.S. Pat. No. 5,345,746 patent allowed a means for controlling how long it takes for sterilization to occur with precision and eliminated the need for testing to be performed during the heating process to check for consistent results and, as such, the wetting of articles as disclosed in U.S. Pat. No. 5,044,141 could be done with uniformity because the amount of anti-bacterial agent being condensed into an aqueous solution, that being the wetting step, upon the articles within the package is consistent or known every time the heat process is performed.

U.S. Pat. No. 5,007,232 disclosed a method comprising the steps of providing a housing with means for providing the passage of a container between the interior and the exterior of the housing, introducing a container into the housing, heating, vaporizing and then dispensing vaporized hydrogen peroxide into the container, dispensing an article into the container, and sealing the container. This method allows for the use of hydrogen peroxide as a sterilant that is easily formed into a vapor at one atmosphere and below the boiling point of liquid hydrogen peroxide and further sterilizes the air with which it is mixed.

U.S. Pat. No. 7,153,471 disclosed a method of decontaminating a structure contaminated by pathogenic microorganisms such as *bacillus anthracis* and its spores, *B. subtilis* var niger and its spores, and *B. stearothermophilus* and its spores including the steps of sealing a contaminated structure sufficiently to enable retention of a gas, introducing methyl bromide gas into sealed contaminated structure to a concentration of methyl bromide in an amount sufficient to deactivate said pathogenic microorganisms and to disable germination of pathogenic bacteria spores, and maintaining said sealed contaminated structure with said concentration of methyl bromide at a sufficient temperature for a sufficient period of time, and deactivating said pathogenic microorganisms and disabling germination of said pathogenic bacteria spores associated with said contaminated structure.

A problem with these processes as claimed and disclosed is that they do not allow for the heating, cooling and humidity control of only the sealed interior of a building which is necessary because attempting to heat, cool or control humidity from the exterior is difficult because buildings are insulated between the interior and exterior walls thereby rejecting heat transfer and humidity infusion or removal. A further problem with these processes as claimed and disclosed is that they do not allow a way to uniformly distribute disinfectant in the interior of a building utilizing a vaporous sterilizing solution because there is no way to regulate the amount of sterilizing agent in the vapor. Another problem is that these processes as claimed and disclosed do not allow for the uniform wetting of articles with controlled amounts of disinfectant and then the removal of the condensed solution and vaporous disinfectant from the interior of the building at atmospheric conditions nor does it allow for the wetting of the surfaces with water after the sterilant is condensed onto the surfaces in order to prevent or lessen any corrosive effects of the residue left behind on the disinfected surfaces. Another problem is that there is no way to prevent any lethal disinfecting gas leaking to the outside of the building from dispersing in the air because it is in the superheated range at one atmosphere.

Despite the great need for an efficient treatment method of reasonable cost that will eradicate microorganisms in the interior surfaces of a building and articles therein, thereby to effectively sterilize said surfaces, the use of regulated vaporous disinfecting agent in aqueous solution by conditioning the air only in the interior of the building and removal there from has not been reported.

BRIEF SUMMARY OF THE INVENTION

The main aspect of this invention concerns a method of distributing a uniform amount of vaporous anti-bacterial agent inside of a building at or about one atmosphere pressure by isolating the interior of the building from the outside environment then conditioning the air inside the building to a specific temperature and humidity usually within the range of 50 to 60 degrees F and 30 to 40 percent relative humidity then introducing a vaporous anti-bacterial agent present in an aqueous solution into the air that is heated to a higher temperature usually to between 80 and 110 degrees F and specific humidity usually between 85 to 95 percent relative humidity for a period of time sufficient to disinfect the air or uniformly distribute vaporous antibacterial agent into it, then cooling and dehumidifying the interior air of the building usually to within the range of 50 to 60 degrees F and between 30 to 40 percent relative humidity until the vaporous anti-bacterial agent present in the air condenses onto the surfaces present inside the building and disinfects it then optionally introducing water vapor into the air that is heated to a higher temperature usually between 80 and 110 degrees F and specific humidity usually between 85 to 95 percent relative humidity then cooling water vapor usually to within the range of 50 to 60 degrees F and between 30 to 40 percent relative humidity onto the surfaces to condense it and to dilute the anti-bacterial agent then heating the air inside the building usually to between 90 and 110 degrees F to evaporate the anti-bacterial agent into the air and then removing it from the interior of the building then conditioning the air inside the building to a specific temperature and humidity usually to within the range of 50 to 60 degrees F and between 30 to 40 percent relative humidity then introducing water vapor into the air that is heated to a higher temperature usually to between 90 and 110 degrees F and specific humidity usually between 85 to 95 percent relative humidity then cooling the interior air usually to within the range of 50 to 60 degrees F and between 30 to 40 percent relative humidity until the water vapor condenses onto the surfaces present inside the building so that any anti-bacterial solution residue on the surfaces is diluted and then heating the air inside the building usually between 90 and 110 degrees F to evaporate the water into the air and then removing it from the interior of the building.

BRIEF DESCRIPTION OF THE SEVERAL VIEWS OF THE DRAWINGS

Not Applicable

DETAILED DESCRIPTION OF THE INVENTION

The present invention comprises methods of using hydrogen peroxide, sodium hypochlorite or any other anti-microbial agent that are in aqueous solution at atmospheric conditions in the decontamination of whole structures or articles that have been contaminated, or may be contaminated, with microorganisms such as bacterial spores. The anti-bacterial agents used in connection with the present method are conventional. Of the numerous agents known to have anti-bacterial properties and which are believed suitable for use in connection with the invention, several have been previously disclosed in the aforementioned U.S. patents. On the basis of this previous disclosure of anti-bacterial agents, it is believed that the following general conditions are applicable.

Example I

Where the anti-bacterial agent is sodium ethylmercurithiosalicylate in aqueous solution, a concentration within the range of 1:100 to 1:2000 has been found effective. After isolating the interior of the building from the outside environment, the air should be brought to a temperature of 50.degrees. F. and humidified to a range of 30% to 40% relative humidity for two hours then introduce said anti-bacterial agent in aqueous solution into the air that is heated to 90 degrees. F. by means of a cool mist humidifier, atomizer or vaporizer and allow it to vaporize until a relative humidity of 95% is attained for a period of 4 hours then cool the interior air of the building to a temperature of 50 degrees. F. and a range of 30% to 40% relative humidity for 2 hours after the vaporous anti-bacterial agent present in the air condenses onto the surfaces present inside the building and disinfects it then heat the air inside the building to 90 degrees. F. for 2 hours after the anti-bacterial agent present on said surfaces evaporates into the air and then remove said vaporous anti-bacterial agent from the interior of the building then bring the interior air to 50 degrees. F and a range of 30% to 40% relative humidity for two hours then introduce water vapor into the air that is heated to 90 degrees F. by means of a cool mist humidifier, atomizer or vaporizer and allow it to vaporize until a relative humidity of 95% is attained then cool the interior of the building to a temperature of 50 degrees F. for 2 hours after condensation onto the interior surfaces to dilute any residue of anti bacterial agent remaining on the surfaces and then heat the air inside the building to 90 degrees F. for two hours after the water on the interior surfaces evaporates into the air and then remove said water vapor from the interior of the building.

Example II

Where the anti-bacterial agent is aqueous iodophor solution, an iodine concentration within the range of 0.0012 to 3.0 percent has been found effective. After isolating the interior of the building from the outside environment, the air should be brought to a temperature of 50.degrees. F. and humidified to a range of 30% to 40% relative humidity for two hours then introduce said anti-bacterial agent in aqueous solution into the air that is heated to 90 degrees. F. by means of a cool mist humidifier, atomizer or vaporizer and allow it to vaporize until a relative humidity of 95% is attained for a period of 4 hours until the air is disinfected then remove said water vapor containing the anti-bacterial agent from the interior of the building.

Example III

Where the anti-bacterial agent is aqueous hydrogen peroxide solution, a hydrogen peroxide concentration of 2.5 to 3.0 percent has been found effective. After isolating the interior of the building from the outside environment, the air should be brought to a temperature of 50.degrees. F. and humidified to a range of 30% to 40% relative humidity for two hours then introduce said anti-bacterial agent in aqueous solution into the air that is heated to 80 degrees. F. by means of a cool mist humidifier, atomizer or vaporizer and allow it to vaporize until a relative humidity of 95% is attained for a period of 4 hours then cool the interior air of the building to a temperature of 50 degrees. F. and a range of 30% to 40% relative humidity for 2 hours after the vaporous anti-bacterial agent present in the air condenses onto the surfaces present inside the building and disinfects it then heat the air inside the building to 80 degrees. F. for 2 hours after the anti-bacterial agent present on said surfaces evaporates into the air and then remove said vaporous anti-bacterial agent from the interior of the building then bring the interior air to 50 degrees. F and a range of 30% to 40% relative humidity for two hours then introduce water vapor into the air that is heated to 90 degrees F. by means of a cool mist humidifier, atomizer or vaporizer and allow it to vaporize until a relative humidity of 95% is attained then cool the interior of the building to a temperature of 50 degrees F. for 2 hours after condensation onto the interior surfaces to dilute any residue of anti bacterial agent remaining on the surfaces and then heat the air inside the building to 90 degrees F. for two hours after the water on the interior surfaces evaporates into the air and then remove said water vapor from the interior of the building.

Example IV

Where the anti-bacterial agent is aqueous sodium hypochlorite solution, a sodium hypochlorite concentration of 2.5 to 5.25 percent has been found effective. After isolating the interior of the building from the outside environment, the air should be brought to a temperature of 50 to 60 degrees. F. and humidified to a range of 30% to 40% relative humidity for two hours then introduce said anti-bacterial agent in aqueous solution by means of a cool mist humidifier, atomizer or vaporizer into the air that is heated to 90 to 104 degrees F. and allow it to vaporize until a relative humidity of 85% to 95% is attained for a period of 1 to 4 hours then cool the interior air of the building to a temperature of 50 to 60 degrees F. and a range of 30% to 40% relative humidity for 1 to 4 hours after the vaporous anti-bacterial agent present in the air condenses onto the surfaces inside the building and disinfects it then bring the interior air to 50 to 60 degrees F and a range of 30% to 40% relative humidity for 1 to 4 hours then introduce water vapor by means of a cool mist humidifier, atomizer or vaporizer into the air that is heated to 90 to 104 degrees F and allow it to vaporize until a relative humidity of 85% to 95% is attained then cool the interior of the building to a temperature of 50 to 60 degrees F for 1 to 4 hours to condense the water vapor onto the interior surfaces to dilute the anti bacterial agent on the surfaces then heat the air inside the building to 90 to 104 degrees F for 1 to 4 hours to allow the anti-bacterial agent present on said surfaces to evaporate into the air and then remove said vaporous anti-bacterial agent from the interior of the building then bring the interior air to 50 to 60 degrees. F and a range of 30% to 40% relative humidity for 1 to 4 hours then introduce water vapor by means of a cool mist humidifier, atomizer or vaporizer into the air that is heated to 90 to 104 degrees F. and allow it to vaporize until a relative humidity of 85% to 95% is attained then cool the interior of the building to a temperature of 50 to 60 degrees F for 1 to 4 hours after condensation onto the interior surfaces to dilute any residue of anti bacterial agent remaining on the surfaces and then heat the air inside the building to 90 to 104 degrees F for 1 to 4 hours after the water on the interior surfaces evaporates into the air and then remove said water vapor from the interior of the building.

Best Mode of the Invention

The interior of a building is sealed then air inside the building is brought to a temperature of 50 degrees F and humidified to 30% relative humidity for two hours then an aqueous solution of sodium hypochlorite with a concentration of 5.25% is vaporized through an atomizer into the air as the air is heated to 100 degrees F until a relative humidity of 90% at 100 degrees F air temperature is attained for 2 hours then cool the interior air to a temperature of 50 degrees F and 30% relative humidity for 2 hours after the anti bacterial agent in the air has condensed onto the surfaces inside the building disinfecting it then water vapor is vaporized through a cool mist dehumidifier as the air is heated to 100 degrees F until a relative humidity of 90% at 100 degrees F interior air temperature is attained for 2 hours then the air is cooled to 50 degrees F and a relative humidity of 30% for 2 hours after the water vapor condenses onto the interior surfaces then the interior air is heated to 100 degrees F for 2 hours until the water and anti bacterial agent evaporates and then the vaporous anti bacterial agent is removed from the interior air then the interior air is cooled to a temperature of 50 degrees F and 30% relative humidity for 2 hours after the anti bacterial agent has been removed from the air then water vapor is vaporized through a cool mist dehumidifier as the air is heated to 100 degrees F until a relative humidity of 90% at 100 degrees F interior air temperature is attained for 2 hours then the air is cooled to 50 degrees F and a relative humidity of 30% for 2 hours after the water vapor has condensed onto the interior surfaces then the interior air is heated to 100 degrees F for 2 hours until the water is evaporated into the air and then the water vapor is removed from the interior air.

What is claimed is:

1. A method of disinfecting and wetting the inside of a building and articles therein at or about one atmospheric pressure comprising the steps of: isolating the interior of the building; then conditioning the air inside of the building to a specific temperature and humidity; then heating said air and introducing any of a number of anti-bacterial agents in aqueous solution into said air until a higher temperature and humidity are achieved causing the air to be disinfected; then cooling the air and antibacterial agent until said air and antimicrobial agent condenses on all of the interior surfaces and disinfects said surfaces; then heating said air and introducing water vapor into said air until a higher temperature and humidity are achieved; then cooling said air until said air condenses on all of the interior surfaces and dilutes the antibacterial agent that is present on said surfaces; then heating said air until the liquid wetting said surfaces evaporates; then removing from the building the antibacterial agent that is present in said air; then heating said air and introducing water vapor into said air until a higher temperature and humidity are achieved; then cooling said air until said air condenses on all of the interior surfaces until the condensation dilutes any residue of anti bacterial agent remaining on the surfaces; then heating said air until the liquid wetting said surfaces evaporates; then removing from the building said residual antibacterial agent that is present in said air condensing.

2. The method of claim 1 in which the anti-bacterial agent is selected from the group consisting of hydrogen peroxide and sodium hypochlorite.

3. A method of disinfecting and wetting the inside of a building and articles therein at or about one atmospheric pressure comprising the steps of: isolating the interior of the building; then conditioning the air inside of the building to a specific temperature and humidity; then heating said air and introducing any of a number of anti-bacterial agents in aqueous solution into said air until a higher temperature and humidity are achieved causing the air to be disinfected; then cooling the air and antibacterial agent until said air and antimicrobial agent condenses on all of the interior surfaces and disinfects said surfaces; then heating said air until the liquid wetting said surfaces evaporates; then removing from the building the antibacterial agent that is present in said air; then heating said air and introducing water vapor into said air until a higher temperature and humidity are achieved; then cooling said air until said air condenses on all of the interior surfaces until the condensation dilutes any residue of anti bacterial agent remaining on the surfaces; then heating said air until the liquid wetting said surfaces evaporates; then removing from the building said residual antibacterial agent that is present in said air condensing.

4. The method of claim 3 in which the anti-bacterial agent is selected from the group consisting of hydrogen peroxide and sodium hypochlorite.

5. A method of disinfecting and wetting the inside of a building and articles therein at or about one atmospheric pressure comprising the steps of: isolating the interior of the building; then conditioning the air inside of the building to a specific temperature and humidity; then heating said air and introducing any of a number of anti-bacterial agents in aqueous solution into said air until a higher temperature and humidity are achieved causing the air to be disinfected; then cooling the air and antibacterial agent until said air and antimicrobial agent condenses on all of the interior surfaces and disinfects said surfaces; then heating said air until the liquid wetting said surfaces evaporates; then removing from the building the antibacterial agent that is present in said air.

6. The method of claim 5 in which the anti-bacterial agent is selected from the group consisting of hydrogen peroxide and sodium hypochlorite.

* * * * *